United States Patent [19]
Baker, Jr. et al.

[11] Patent Number: 6,015,832
[45] Date of Patent: Jan. 18, 2000

[54] METHODS OF INACTIVATING BACTERIA INCLUDING BACTERIAL SPORES

[75] Inventors: James R. Baker, Jr., Ann Arbor, Mich.; D. Craig Wright, Gaithersburg, Md.; Michael M. Hayes; Tarek Hamouda, both of Ypsilanti, Mich.; Joan Brisker, Silver Spring, Md.

[73] Assignee: The Regents of the University of Michigan, Ann Arbor, Mich.

[21] Appl. No.: 09/002,228

[22] Filed: Dec. 31, 1997

[51] Int. Cl.[7] .......................... A61K 31/22; A61K 31/225
[52] U.S. Cl. .......................... 514/546; 514/547; 514/548; 514/549; 514/938; 514/939; 514/943
[58] Field of Search ..................... 514/546, 547, 514/548, 549, 938, 939, 943

[56] References Cited

U.S. PATENT DOCUMENTS

| | | | |
|---|---|---|---|
| 4,020,183 | 4/1977 | Asculai et al. | 424/341 |
| 4,540,573 | 9/1985 | Neurath et al. | 424/85 |
| 4,909,940 | 3/1990 | Horowitz et al. | 210/634 |
| 5,186,945 | 2/1993 | Shanbrom | 424/529 |
| 5,547,677 | 8/1996 | Wright | 424/401 |
| 5,549,901 | 8/1996 | Wright | 424/401 |
| 5,618,840 | 4/1997 | Wright | 514/549 |

FOREIGN PATENT DOCUMENTS 9633725  10/1996  WIPO.

OTHER PUBLICATIONS

Gennaro, A.R. et al., "Remington's Pharmaceutical Sciences," published by Philadelphia College of Pharmacy and Science (Philadelphia, PA) pp. 1295, 1301–1302 (1985).

Smyth, H.F. Jr. et al., "The Place of the Range Finding Test in the Industrial Toxicology Laboratory," Journal of Industrial Hygiene and Toxicology 26(8):269–273 (1944).

Windholtz, M. et al., "The Merck Index," published by Merck & Co. (Rahway, NJ) p. 1249, Abstract No. 8574 (1983).

Baker, James R. Jr. et al., "Molecular Decoys to Soak up Pathogens," Defense Sciences Office Web Page (Biological Warfare Defense) 1 page.

*Primary Examiner*—Kevin E. Weddington
*Attorney, Agent, or Firm*—Brinks Hofer Gilson & Lione

[57] ABSTRACT

Methods for inactivating bacteria including bacterial spores using an oil-in-water emulsion are provided. The oil-in-water emulsion comprises an oil, a surfactant and an organic phosphate-based solvent. These methods can be used to inactivate a wide variety of bacteria such as Bacillus.

48 Claims, 2 Drawing Sheets

Time Zero 1 hour  2 hours  4 hours 1 hour  2 hours  4 hours  6 hours

METHODS OF INACTIVATING BACTERIA INCLUDING BACTERIAL SPORES

SPONSORSHIP

Work on this invention was supported, in part, by DARPA contract MDA972-97-1-0007.The government may have certain rights in this invention.

FIELD OF THE INVENTION

The present invention relates to methods of inactivating bacteria including spores by contacting the bacteria with an oil-in-water emulsion which inactivates bacteria upon contact.

BACKGROUND OF THE INVENTION

It is known that if a water-immiscible lipid phase is mixed into an aqueous phase by mechanical agitation, for example, by means of an ultra-disperser, a dispersion, such as an oil-in-water emulsion, will develop. The stability of the resulting dispersion may require the addition of an emulsifying agent, the molecules of which are adsorbed onto the oil/water interface to form a kind of continuous membrane which prevents direct contact between two adjacent droplets. One advantage of oil-in-water emulsions is that they may readily be diluted with water to a desired composition.

In addition to discrete oil droplets dispersed in an aqueous phase, oil-in-water emulsions can also contain other lipid structures, such as small lipid vesicles (i.e., lipid spheres which often consist of several substantially concentric lipid bilayers separated from each other by layers of aqueous phase), micelles (i.e., amphiphile molecules in small clusters of 50–200 molecules arranged so that the polar head groups face outward toward the aqueous phase and the apolar tails are sequestered inward away from the aqueous phase), or lamellar phases (lipid dispersions in which each particle consists of parallel amphiphile bilayers separated by thin films of water). These lipid structures are formed as a result of hydrophobic forces which drive apolar residues (i.e., long hydrocarbon chains) away from water.

The portals of entry of pathogenic bacteria are predominantly the skin and mucus membranes. The first step in many infections is attachment or colonization on skin or mucus membranes, followed by subsequent invasion and dissemination of the infectious pathogen. Accordingly, it is desirable to provide a bacteria-inactivating formulation and methods of using such formulations to inactivate bacteria.

In addition, many types of bacteria form highly resistant, thick-walled endospores also referred to as spores, in response to unfavorable conditions, which resume their metabolic activities when conditions improve. These dehydrated bodies contain the cellular components held in a state of dormancy, ready to absorb water and resume their activities. It would thus be desirable to provide bacterial spore-inactivating formulations and methods of using the formulations to inactivate bacterial spores.

Bacteria, including spores, can be inactivated by heat, pressure and the use of chemical agents often referred to as bacteriocides. For example, corrosive compositions, e.g., formaldehyde and sodium hypochlorite (bleach), have been used to inactivate spores. Unfortunately, such compositions are toxic or irritating to skin and mucus membranes. It would therefore be desirable to provide compositions and methods for inactivating bacteria including bacterial spores, which are non-toxic to skin and mucus membranes. It would also be desirable to provide compositions and methods for inactivating bacteria and bacterial spores which are effective in vivo.

Accordingly, an object of the present invention is to provide a method of inactivating bacteria, including spores, by contacting the bacteria with a bacteria-inactivating emulsion.

It is a further object of the invention to provide a non-toxic, non-irritating preparation and method of using same that inactivates bacteria including spores, upon contact.

Another object of the present invention is to provide a method of preventing bacterial infection in an affected subject by administering a bacteria-inactivating emulsion to the subject.

SUMMARY OF THE INVENTION

The present invention provides a method of inactivating bacteria, where the method includes the steps of providing a bacteria-inactivating emulsion and contacting the bacteria with the emulsion. The emulsion is an oil-in-water emulsion comprising a surfactant, an organic phosphate based solvent, and a carrier oil. In one embodiment, the bacteria is a gram positive bacteria, i.e., bacteria with dense peptidoglycan walls which readily absorb a purple dye (crystal violet) in a process referred to as Gram's stain. In certain preferred embodiments, the gram positive bacteria or bacterial spores are Bacillus. In a particularly preferred embodiment, the bacteria or spores are *Bacillus anthracis*.

In another embodiment, the bacteria is a gram negative bacteria, i.e., bacteria which do not readily absorb the purple dye in a Gram's stain. In this embodiment, the bacteria-inactivating emulsion is premixed with a compound capable of increasing the uptake of the emulsion by the cell wall. In certain preferred embodiments, the compound is a chelating agent, e.g., ethylenediaminetetraacetic acid (EDTA), a solvent e.g., dimethyl sulfoxide (DMSO), a detergent, e.g., sodium dodecyl sulfate (SDS), and combinations thereof. In other preferred embodiments, the compounds in combination with peptides are used to increase the uptake of the emulsions by the cell wall, e.g., dipeptide and oligopeptide permeases, diglycine, triglycine, mixtures thereof, or other oligopeptides.

The emulsion used in the methods of the present invention consists primarily of droplets of an oily discontinuous phase dispersed in an aqueous continuous phase, such as water. The discontinuous phase is prepared from a surfactant, an oil carrier, and an organic phosphate-based solvent such as tri-n-butyl phosphate. The emulsions are highly stable, and are not decomposed even after long storage periods.

The bacteria-inactivating emulsions are non-toxic and safe when swallowed, inhaled, or applied to the skin. This is in contrast to chemical microbicides which are known irritants. The bacteria-inactivating emulsions also appear to be non-toxic to plants.

Oils useful in forming oil-in-water emulsions include a broad spectrum of water-immiscible materials, such as soybean oil, avocado oil, squalene oil, other fish oils, squalane oil, sesame oil, olive oil, canola oil, corn oil, rapeseed oil, safflower oil, sunflower oil, flavor oils, and mixtures thereof.

Surfactants useful in forming the emulsions used in the methods of the present invention include a variety of anionic and nonionic surfactants, as well as other emulsifiers capable of promoting the formation of oil-in-water emulsions. In general, the emulsifier will be relatively hydrophilic, and blends of emulsifiers can be used to achieve the necessary qualities. Nonionic surfactants have advantages over ionic emulsifiers: they are compatible with a broad pH range and often form more stable emulsions than do ionic (e.g., soap-type) emulsifiers. Particularly useful surfactants include the detergents sold under the trademarks Tween 20, Tween 80, and the phenoxypolyethoxyethanols like Triton (i.e., X-100). A most preferred surfactant is Triton X-100 (t-octylphenoxypolyethoxyethanol).

Organic phosphate-based solvents useful in forming the oil-in-water emulsions include dialkyl and trialkyl phosphates. In a preferred embodiment, each alkyl group of the di- or trialkyl phosphate has one to ten carbon atoms, more preferably two to eight carbon atoms. The alkyl groups of the di- or trialkyl phosphate can all be the same or can be different. A particularly preferred trialkyl phosphate is tri-n-butyl phosphate, which is a plasticizer. Mixtures of different dialkyl and trialkyl phosphates can be employed. In addition, alcohols may be employed as a solvent, e.g., octanol.

In another embodiment of the invention, at least a portion of the emulsion may be in the form of lipid structures including, but not limited to, unilamellar, multilamellar, and paucilamellar lipid vesicles, micelles, and lamellar phases.

The present invention also provides methods of treating a subject by applying a bacteria-inactivating preparation suitable for pharmaceutical administration, which may also include a pharmaceutically acceptable carrier. The preparation can be applied topically to skin surface areas, mucus membranes, or oral surfaces, for example, as a cream, gel, spray, or mouthwash, to treat or prevent bacterial infections. The preparation can also be applied to wounds caused by bacterial infection. Accordingly, the present invention further provides a method for inactivating a bacteria, including bacterial spores, by topical application of the emulsions described herein.

In a further embodiment, the invention includes methods of preventing bacterial infection in a subject by applying the emulsion described herein to the skin or mucous membrane of the subject to inactivate the bacteria or spores. By inactivating bacteria or spores before attachment or colonization, subsequent invasion and dissemination of the infectious pathogen may be prevented.

In an additional embodiment, the invention includes methods of decontamination, i.e., inactivating bacteria and particularly spores found on any surface. Surfaces which will likely come in contact with a human, e.g., vehicles, equipment, instruments, etc., may thus be decontaminated by applying the emulsions described herein to the surfaces.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

DETAILED DESCRIPTION OF THE INVENTION

Figure 1:
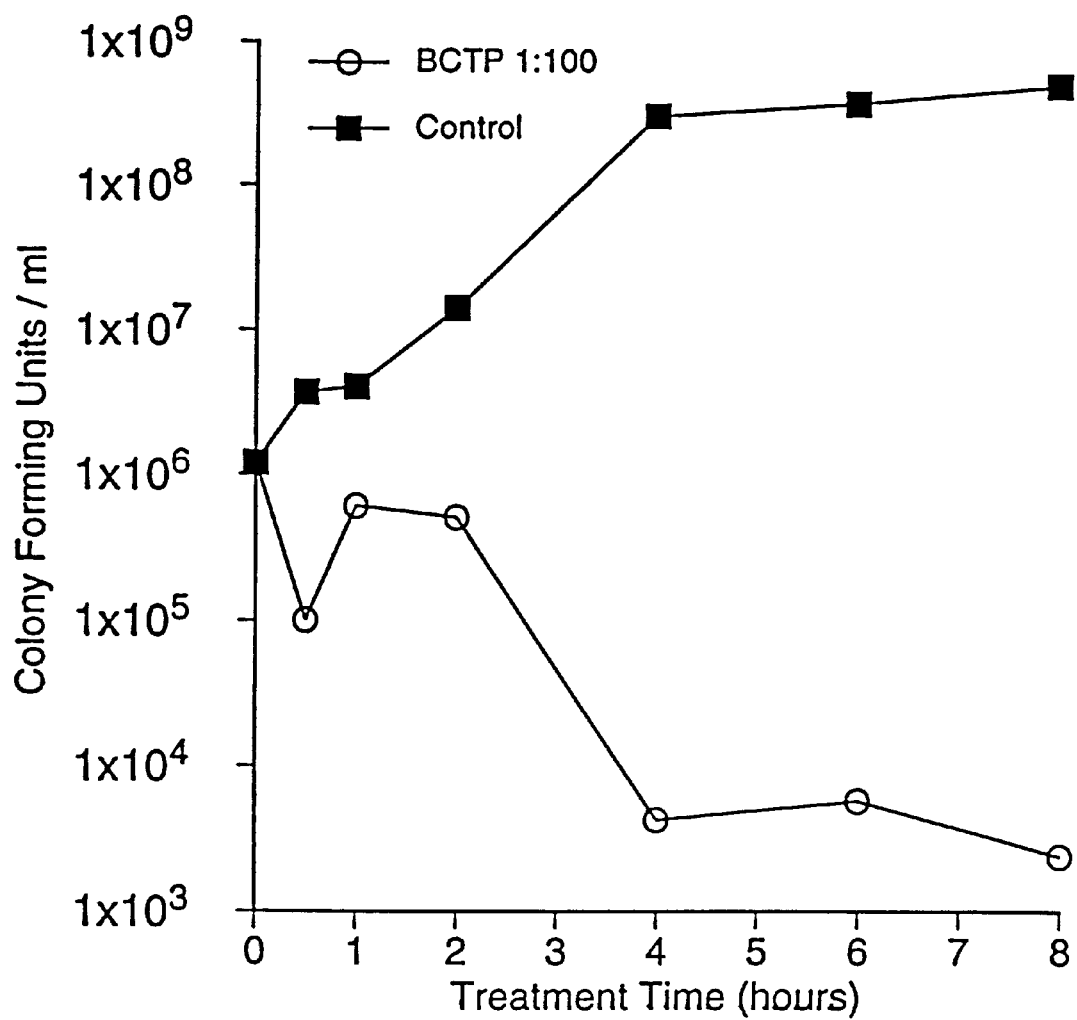
FIG. 1 is a graph showing the bactericidal efficacy of an emulsion of the present invention on *B. cereus* spores.

The present invention relates to methods of inactivating bacteria including pores by contacting the bacteria with oil-in-water emulsions made up of droplets of an oily discontinuous phase containing an organic phosphate-based solvent dispersed in an aqueous continuous phase, and a surfactant. The emulsions are stable, non-toxic, and simple and inexpensive to formulate.

The term "bacteria-inactivating", as used herein, means having the ability to kill bacteria or spores on contact. It appears that inactivation is achieved by surfactant and solvent interactions with bacteria cell membranes, thereby disrupting the cell membrane and causing cell death. Accordingly, one aspect of the present invention provides a method of applying a bacteria-inactivating oil-in-water emulsion which contains materials capable of interacting with the bacterial membrane or spore and disrupting the structure so that the bacteria or spore is inactivated.

As described in more detail in Specific Example 2, infra, the methods of the present invention can rapidly inactivate gram positive bacteria. In preferred embodiments, the inactivation of bacteria occurs after no more than six hours, more preferably after no more than two hours, and even more preferably in less than one hour after the bacteria is contacted with an emulsion according to the present invention.

As described in more detail in Specific Example 3, infra, the methods of the invention can also rapidly inactivate certain gram negative bacteria. In such methods, the bacteria-inactivating emulsions are premixed with a compound which increases the uptake of the emulsion by the cell wall. For example, compounds such as EDTA, DMSO and SDS are effective when mixed with the emulsions in increasing the uptake of the emulsions by the cell wall. Oligopeptides such as diglycine and triglycine may also be employed as cell wall uptake enhancers. It should be noted that the emulsion and cell wall uptake enhancer are effective against certain Gram positive and negative bacteria but are not effective against all Gram negative bacteria and thus may be administered orally where they will come in contact with necessary gut bacteria, without unacceptable adverse effects to the subject's colonic microflora (i.e., *E. coli*).

As described in more detail in Specific Example 4, infra, the methods of the present invention can also inactivate a bacterial spore. In preferred embodiments, the inactivation occurs no more than six hours, more preferably no more than four hours, after the spore is contacted with the emulsion.

As set forth in detail in Specific Example 5, infra, the methods of the present invention are effective in inactivating bacteria including spores in vivo, without significant toxicity.

Also, as further described in Specific Examples 6 and 7, infra the bacteria-inactivating methods of the present invention are non-toxic, e.g., the emulsions may be applied topically and orally and have an acceptable toxicity profile.

The term "emulsion", as used herein, includes classic oil-in-water dispersions or droplets, as well as other lipid structures which can form as a result of hydrophobic forces which drive apolar residues (i.e., long hydrocarbon chains) away from water and drive polar head groups toward water, when a water immiscible oily phase is mixed with an aqueous phase. These other lipid structures include, but are not limited to, unilamellar, paucilamellar, and multilamellar lipid vesicles, micelles, and lamellar phases.

The bacteria-inactivating oil-in-water emulsions used in the methods of the present invention can be formed using classic emulsion forming techniques known in the art. In brief, the oily phase is mixed with the aqueous phase under relatively high shear forces to obtain an oil-in-water emulsion containing oil droplets which are approximately 1–2 microns in diameter. The oily discontinuous phase is formed by blending (a) an oil carrier; (b) a surfactant; and (c) an organic phosphate-based solvent. The emulsion is formed by blending the oily phase with an aqueous phase (e.g., water) on a volume-to-volume basis ranging from about 1:4 to 4:1, preferably about 1:4 oily phase to aqueous phase. The oil and aqueous phases can be blended using any apparatus capable of producing shear forces sufficient to form an emulsion (e.g., French Press or commercial high shear mixers).

The bacteria-inactivating oil-in-water emulsions used in the methods of the present invention can be used to inactivate a variety of bacteria and bacterial spores upon contact. For example, the presently disclosed emulsions can be used to inactivate Bacillus including *B. cereus, B. circulans, B. megaterium* and *B. subtilus,* also including Clostridium, e.g., *C. botulinum* and *C. tetani*. The methods of the present invention may be particularly useful in inactivating certain biological warfare agents, e.g., *B. anthracis.*

The bacteria-inactivating emulsion described herein may be used as a preparation suitable for pharmaceutical administration. Such preparation may comprise an oil-in-water emulsion of the present invention and a pharmaceutically acceptable carrier. The term "pharmaceutically acceptable carrier", as used herein, refers to any physiologically compatible carrier for stabilizing emulsions of the present invention for pharmaceutical administration. Use of such media and agents for pharmaceutically active substances is well known in the art. Except insofar as any conventional media or agent is incompatible with the emulsions of the present invention, use thereof in a pharmaceutical preparation is contemplated.

The present invention further provides methods for inactivating bacteria by topical and/or oral administration of an oil-in-water emulsion of the present invention, preferably in the form of a pharmaceutical preparation. The term "topical", as used herein, includes, without limitation, application to mucous membranes, oral surfaces, skin, including wounds, and the surfaces of any bodily orifice, such as the nasal cavity, vagina or rectum. The term "oral", as used herein includes, without limitation, application by swallowing by the subject. It will be appreciated that the emulsions may be combined with other edible substances for swallowing by the subject.

The specific examples below further describe the compositions and methods of the present invention. These examples are for illustrative purposes only and are not intended in any way to limit the scope of the invention.

SPECIFIC EXAMPLE 1

In this example, a bacteria-inactivating oil-in-water emulsion containing a surfactant and a trialkyl phosphate, was formed and characterized.

The emulsion was formed as follows: an oil phase was made by blending tributyl phosphate, soybean oil, and a surfactant (e.g., Triton X-100) and then heating the resulting mixture at 86° C. for one hour. An emulsion was then produced by injecting water into the oil phase at a volume/volume ratio of one part oil phase to four parts water. The emulsion can be produced manually, with reciprocating syringe instrumentation, or with batch or continuous flow instrumentation. Table 1 shows the proportions of each component, the pH, and the size of the emulsion as measured on a Coulter LS 130 laser sizing instrument equipped with a circulating water bath.

Table 1

| Chemical Components of Emulsion | Percentage of Each Component | pH | Mean Coulter Size (in Microns) | Mean Coulter Range (in Microns) |
|---|---|---|---|---|
| BCTP | | | | |
| Triton X-100 | 2% | 5.16 | 1.074 | 0.758–1.428 |
| Tributyl phosphate | 2% | | | |
| Oil (ex. Soy bean) | 16% | | | |
| Water | 80% | | | |
| BCTP 0.1† | | | | |
| Triton X-100 | 0.20% | 5.37 | 0.944 | 0.625–1.333 |
| Tributyl phosphate | 0.20% | | | |
| Oil (ex. Soy bean) | 1.60% | | | |
| Water | 98% | | | |

† This emulsion was obtained by diluting the BCTP emulsion with water in a ratio of 1:9.

The emulsions of the present invention are highly stable. The BCTP and BCTP 0.1, emulsions have been found to be substantially unchanged after storage at room temperature for at least 24 months.

SPECIFIC EXAMPLE 2

In Vitro Bactericidal Efficacy Study I—Gram Positive Bacteria

In order to study the bactericidal efficacy of the emulsions of the present invention, the emulsions were mixed with various bacteria for 10 minutes and then plated on standard microbiological media at varying dilutions. Colony counts were then compared to untreated cultures to determine the percent of bacteria killed by the treatment. Table 2 summarizes the results of the experiment.

TABLE 2

| Organism | Inoculum (CFU) | % Killing | Emulsion Tested |
|---|---|---|---|
| *Vibrio cholerae* | $1.3 \times 10^8$ | 100 | BCTP |
| *Vibrio cholerae* Eltor | $5.1 \times 10^8$ | 100 | BCTP |
| *Vibrio parahemolytica* | $4.0 \times 10^7$ | 98–100 | BCTP |

In order to study the bactericidal effect of the emulsions of the present invention on various vegetative forms of Bacillus species, an emulsion at three dilutions was mixed with four Bacillus species for 10 minutes and then plated on microbiological medium. Colony counts were then compared with untreated cultures to determine the percent of bacteria killed by the treatment. Table 3 contains a summary of the bactericidal results from several experiments with the mean percentage kill in parenthesis.

TABLE 3

| BCTP/ Dilution | *B. cereus* | *B. circulans* | *B. megaterium* | *B. subtilus* |
|---|---|---|---|---|
| 1:10 | 99% (99) | 95–99% (97%) | 99% (99) | 99% (99) |
| 1:100 | 97–99% (98%) | 74–93% (84%) | 96–97% (96%) | 99% (99) |
| 1:1000 | 0% (0) | 45–60% (52%) | 0–32% (16%) | 0–39% (20%) |

SPECIFIC EXAMPLE 3

In Vitro Bactericidal Efficacy Study II—Gram Negative Bacteria

To increase the uptake of the bacteria-inactivating emulsions by the cell walls of gram negative bacteria, thereby enhancing the microbicidal effect of the emulsions on the resistant gram negative bacteria, EDTA (ethylenediaminetetraacetic acid) was premixed with the emulsions. The EDTA was used in low concentration (50–250 $\mu$M) and the mix was incubated with the various gram negative bacteria for 15 minutes. The microbicidal effect of the mix was then measured on Trypticase soy broth. The results are set forth in Table 4 below. There was over 99% reduction of the bacterial count using BCTP in 1/100 dilutions. This reduction of count was not due to the killing effect of EDTA alone as shown from the control group in which 250 $\mu$M of EDTA alone could not reduce the bacterial count in 15 minutes.

TABLE 4

| Bacterium | Bacteria alone (CFU) | Bacteria + BCTP (CFU) | Bacteria + BCTP + EDTA (CFU) | Bacteria + EDTA (CFU) |
|---|---|---|---|---|
| S. typhimurium | 1,830,000 | 1,370,000 | 40 | 790,000 |
| S dysenteriae | 910,000 | 690,000 | 0 | 320,000 |

The addition of very small amounts of other substances such as dimethyl sulfoxide (DMSO) or sodium dodecyl sulfate (SDS) also increases the uptake of the emulsions into the cells, thereby enhancing the microbicidal effect.

Studies are performed to show the enhanced microbicidal effect of mixtures of the emulsions and diglycine or triglycine, to increase the uptake of the emulsions by the cell wall using the bacterial enzymes dipeptide and polypeptide permeases.

SPECIFIC EXAMPLE 4

In Vitro Bactericidal Efficacy Study III—Vegetative and Spore Forms

Bacillus cereus (B. cereus, ATCC #14579), was utilized as a model system for Bacillus anthracis. Experiments with BCTP diluted preparations to study the bactericidal effect of the compounds of the present invention on the vegetative form (actively growing) of B. cereus were performed. Treatment in medium for 10 minutes at 37° C. was evaluated. As summarized in Table 5, the BCTP emulsion is efficacious against the vegetative form of B. cereus. A 10 minute exposure with this preparation is sufficient for virtually complete killing of vegetative forms of B. cereus at all concentrations tested including dilutions as high as 1:100.

TABLE 5

| Emulsion | Undiluted | 1:10 | 1:100 |
|---|---|---|---|
| BCTP | >99% | >99% | 59–>99% |
|  | Avg = >99% | Avg = >99% | Avg = 82% |

Number of experiments = 4

The spore form of B. anthracis is one of the most likely organisms to be used as a biological weapon. Spores are well known to be highly resistant to most disinfectants. As describe above, effective killing of spores usually requires the use of toxic and irritating chemicals such as formaldehyde or sodium hypochlorite (i.e., bleach). The same experiment was therefore performed with the spore form of B. cereus. As shown in Table 6, treatment in both medium for 10 minutes at 37° C. was not sufficient to kill B. cereus spores.

TABLE 6

| Emulsion | Undiluted | 1:10 | 1:100 |
|---|---|---|---|
| BCTP | 0%–12% | 0% | 0% |
|  | Avg = 6% | Avg = 0% | Avg = 0% |

Number of experiments = 2

To evaluate the efficacy of the compounds of the present invention on the spore form of B. cereus over a period of time, BCTP was incorporated into solid agar medium at 1:100 dilution and the spores spread uniformly on the surface and incubated for 96 hours at 37° C. No growth occurred on solid agar medium wherein BCTP had been incorporated, out to 96 hours (i.e., >99% killing, average >99% killing, 3 experiments).

Figure 2A:
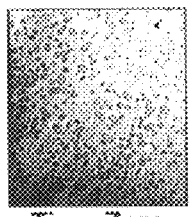
FIGS. 2A–2C are photographs of bacterial smears showing the bactericidal efficacy of an emulsion of the present invention on *B. cereus* spores.
Figure 2B:
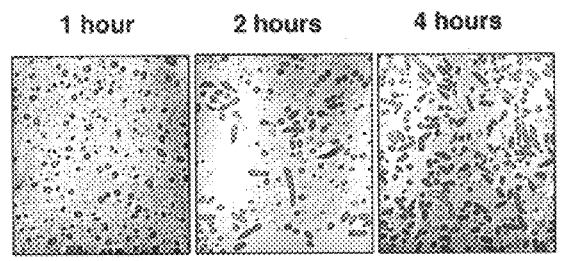
Figure 2C:
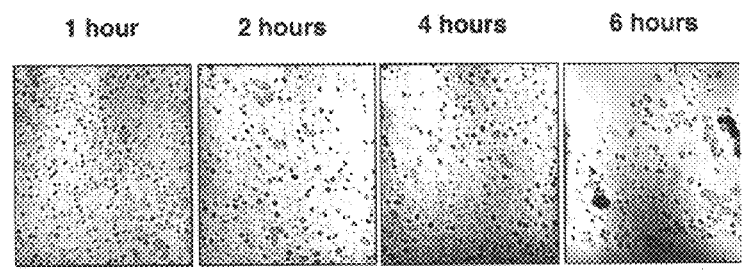

In an attempt to more closely define the time at which killing of spores by BCTP occurred, the following experiment was performed. Briefly, a spore preparation was treated with BCTP at a dilution of 1:100 and compared to an untreated control. The number of colony forming units per milliliter (CFU/ml) was quantitated after 0.5, 1, 2, 4, 6, and 8 hours. As shown in FIG. 1, CFU/ml in the untreated control increased over the first 4 hours of incubation and then reached a plateau. Bacterial smears prepared at time zero, 1, 2, 4 and 6 hours, and stained for spore structures, revealed that by 2 hours no spore structures remained (FIGS. 2A–2C). Thus, 100% germination of spores occurred in the untreated control by the 2 hour time point. In the spore preparation treated with BCTP, CFU/ml showed no increase over the first 2 hours and then declined rapidly over the time period from 2–4 hours. The decline from baseline CFU/ml over 2–4 hours was approximately 1000-fold. Bacterial smears prepared at the same time points and stained for spore structures revealed that spore structures remained to the end of the experiment at 8 hours. Hence, germination of spores did not occur in the BCTP treated culture due to either inhibition of the germination process or because the spores were damaged and unable to germinate.

In order to determine whether the emulsions were effective in killing other Bacillus species in addition to B. cereus, a similar experiment was performed as described above, wherein spore preparations were treated with emulsions and compared to an untreated control after four hours of incubation. The following table shows the results wherein the numbers represent a range of results from several experiments with the average in parenthesis.

TABLE 7

| BCTP/ Dilution | B. cereus | B. circulans | B. megaterium | B. subtilus |
|---|---|---|---|---|
| 1:10 | 71–93% (82) | 30–77% (61%) | 80–99% (93%) | 5–90% (31%) |
| 1:100 | 87–95% (96) | 23–82% (61%) | 74–99% (92%) | 0–87% (39%) |
| 1:1000 | 0–94% (47) | 20–79% (55%) | 90–97% (94%) | 0–87% (22%) |

SPECIFIC EXAMPLE 5

In Vivo Bactericidal Efficacy Study

Bacillus cereus was passed three times on blood agar (TSA with 5% sheep blood, REMEL). B. cereus was scraped from the third passage plate and resuspended in Trypticase soy broth (TSB) (available from BBL). The *B. cereus* suspension was divided into two tubes. An equal volume of sterile saline was added to one tube and mixed. 0.1 cc of the *B. cereus* suspension/saline was injected subcutaneously into 5 CD-1 mice. An equal volume of BCTP (diluted 1:5 in sterile saline) was added to one tube and mixed, giving a final dilution of BCTP at 1:10. The *B. cereus* suspension/BCTP was incubated at 37° C. for 10 minutes while being mixed. 0.1 cc of the *B. cereus* suspension/BCTP was injected subcutaneously into 5 CD-1 mice. Equal volumes of BCTP (diluted 1:5 in sterile saline) and TSB were mixed, giving a final dilution of BCTP at 1:10. 0.1 cc of the BCTP/TSB was injected subcutaneously into 5 CD-1 mice.

The number of colony forming units (cfu) of *B. cereus* in the inocula were quantitated as follows: 10-fold serial dilutions of the *B. cereus* and *B. cereus*/BCTP suspensions were made in distilled $H_2O$. Duplicate plates of TSA were inoculated from each dilution (10 ul per plate). The TSA plates were incubated overnight at 37° C. Colony counts were made and the number of cfu/cc was calculated. Necrotic lesions appears to be smaller in mice which were inoculated with *B. cereus* which was pretreated with BCTP. The following table shows the results of the experiment.

TABLE 8

| Inoculum | ID # | Observation (24 hours) |
|---|---|---|
| *B. cereus* | 1528 | necrosis at injection site |
| $3.1 \times 10^7$ | 1529 | necrosis at injection site |
| cfu/mouse | 1530 | dead |
| | 1531 | dead |
| | 1532 | necrosis at injection site |
| *B. cereus* | 1348 | necrosis at injection site |
| $8.0 \times 10^5$ | 1349 | no reaction |
| cfu/mouse | 1360 | no reaction |
| (BCTP treated) | 1526 | necrosis at injection site |
| | 1527 | necrosis at injection site |
| BCTP/TSB | 1326 | no reaction |
| | 1400 | no reaction |
| | 1375 | no reaction |
| | 1346 | no reaction |
| | 1347 | no reaction |

*Bacillus cereus* was grown on Nutrient Agar (Difco) with 0.1% Yeast Extract (Difco) and 50 ug/ml $MnSO_4$ for induction of spore formation. The plate was scraped and suspended in sterile 50% ethanol and incubated at room temperature for 2 hours with agitation in order to lyse remaining vegetative bacteria. The suspension was centrifuged at 2,500×g for 20 minutes and the supernatant discarded. The pellet was resuspended in di$H_2O$, centrifuged at 2,500×g for 20 minutes, and the supernatant discarded. The spore suspension was divided. The pellet was resuspended in TSB. 0.1 cc of the *B. cereus* spore suspension diluted 1:2 with saline was injected subcutaneously into 3 CD-1 mice. Equal volumes of BCTP (diluted 1:5 in sterile saline) and *B. cereus* spore suspension were mixed, giving a final dilution of BCTP at 1:10 (preincubation time). 0.1 cc of the BCTP/*B. cereus* spore suspension was injected subcutaneously into 3 CD-1 mice.

The number of colony forming units (cfu) of *B. cereus* in the inoculum was quanitated as follows. 10-fold serial dilutions of the *B. cereus* and *B. cereus*/BCTP suspensions were made in distilled $H_2O$. Duplicate plates of TSA were inoculated from each dilution (10 ul per plate). The TSA plates were incubated overnight at 37° C. Colony counts were made and the number of cfu/cc was calculated. Necrotic lesions appeared to be smaller in mice which were inoculated with *B. cereus* spores which were pretreated with BCTP.

TABLE 9

| Inoculum | Observation (24 hours) |
|---|---|
| *B. cereus* $6.4 \times 10^6$ spores/mouse | 2/3 (66%) mice exhibited necrosis at injection site |
| *B. cereus* $4.8 \times 10^6$ spores/mouse (BCTP treated) | 1/3 (33%) mice exhibited necrosis at injection site |
| *B. cereus* $4.8 \times 10^6$ vegetative forms/mouse | 3/3 (100%) mice exhibited necrosis at injection site |
| Lysed *B. cereus* $4.8 \times 10^6$ cfu/mouse | 3/3 (100%) mice did not exhibit symptoms |
| BCTP/TSB | 1/3 (33%) mice appeared to have some skin necrosis |

*Bacillus cereus* was grown on Nutrient Agar (Difco) with 0.1% Yeast Extract (Difco) and 50 ug/ml $MnSO_4$ for induction of spore formation. The plate was scraped and suspended in sterile 50% ethanol and incubated at room temperature for 2 hours with agitation in order to lyse remaining vegetative bacteria. The suspension was centrifuged at 2,500×g for 20 minutes and the supernatant discarded. The pellet was resuspended in distilled $H_2O$, centrifuged at 2,500×g for 20 minutes, and the supernatant discarded. The pellet was resuspended in TSB. The *B. cereus* spore suspension was divided into three tubes. An equal volume of sterile saline was added to one tube and mixed. 0.1 cc of the *B. cereus* suspension/saline was injected subcutaneously into 10 CD-1 mice. An equal volume of BCTP (diluted 1:5 in sterile saline) was added to the second tube and mixed, giving a final dilution of BCTP at 1:10. The *B. cereus* spore suspension/BCTP (1:10) was incubated at 37° C. for 4 hours while being mixed. 0.1 cc of the *B. cereus* spore suspension/BCTP (1:10) was injected subcutaneously into 10 CD-1 mice. An equal volume of BCTP (diluted 1:50 in sterile saline) was added to the third tube and mixed, giving a final dilution of BCTP at 1:100. The *B. cereus* spore suspension/BCTP (1:100) was incubated at 37° C. for 4 hours while being mixed. 0.1 cc of the *B. cereus* spore suspension/BCTP (1:100) was injected subcutaneously into 10 CD-1 mice. Equal volumes of BCTP (diluted 1:5 in sterile saline) and TSB were mixed, giving a final dilution of BCTP at 1:10. 0.1 cc of the BCTP/TSB was injected subcutaneously into 10 CD-1 mice. Equal volumes of BCTP (diluted 1:50 in sterile saline) and TSB were mixed, giving a final dilution of BCTP at 1:100. 0.1 cc of the BCTP/TSB was injected subcutaneously into 10 CD-1mice.

TABLE 10

| Inoculum sc | ID # | Observation at 24 hours |
|---|---|---|
| *B. cereus* | 1 | 2.4 $cm^2$ skin lesion with 0.08 $cm^2$ necrotic area |
| $5.5 \times 10^7$ spores/mouse | 2 | no abnormalities observed |
| No treatment group | 3 | Moribund with 8 $cm^2$ skin lesion and hind limb paralysis |
| | 4 | 3.52 $cm^2$ skin lesion |
| | 5 | 1.44 $cm^2$ skin lesion |
| | 6 | 3.4 $cm^2$ skin lesion |
| | 7 | 5.5 $cm^2$ skin lesion |
| | 8 | 5.5 $cm^2$ skin lesion |

TABLE 10-continued

| Inoculum sc | ID # | Observation at 24 hours |
|---|---|---|
| | 9 | 3.3 $cm^2$ skin lesion with 0.72 $cm^2$ necrotic area |
| | 10 | 2.64 $cm^2$ skin lesion with two necrotic areas (0.33 $cm^2$ and 0.1 $cm^2$) Mean lesion size in Spore group alone = 3.97 $cm^2$ [1/10 (10%) with no abnormalities observed] |

Note: Skin lesions grey in color with edema, necrotic areas red/dry.

TABLE 11

| Inoculum sc | ID # | Observation at 24 hours |
|---|---|---|
| *B. cereus* | 41 | no abnormalities observed |
| 2.8 × $10^7$ | 42 | no abnormalities observed |
| spores/mouse | 43 | 1.2 $cm^2$ white skin lesion with grey center, |
| in the | | slight edema |
| BCTP 1:10 | 44 | 0.78 $cm^2$ white skin lesion |
| | 45 | 0.13 $cm^2$ white skin lesion |
| treated group | 46 | 2.2 $cm^2$ white skin lesion |
| | 47 | 1.8 $cm^2$ white skin lesion with 0.1 cm brown area in center |
| | 48 | 1 $cm^2$ white skin lesion with grey center |
| | 49 | 0.78 $cm^2$ white skin lesion |
| | 50 | no abnormalities observed Mean lesion size in BCTP 1:10 treatment group = 113 $cm^2$ [3/10 (30%) with no abnormalities observed] |
| *B. cereus* | 51 | 2.1 $cm^2$ grey skin lesion |
| 1.8 × $10^7$ | 52 | 0.72 $cm^2$ grey skin lesion |
| spores/mouse | 53 | 1.5 $cm^2$ grey skin lesion |
| in the | 54 | 1.2 $cm^2$ grey skin lesion |
| BCTP 1:100 | 55 | 3.15 $cm^2$ grey skin lesion |
| treated group | 56 | 0.6 $cm^2$ grey skin lesion |
| | 57 | 0.5 $cm^2$ grey skin lesion |
| | 58 | 2.25 $cm^2$ grey skin lesion |
| | 59 | 4.8 $cm^2$ grey skin lesion with necrotic area 1 cm diameter |
| | 60 | 2.7 $cm^2$ grey skin lesion Mean lesion size in BCTP 1:100 treatment group = 1.9 $cm^2$ [0/10 (0%) with no abnormalities observed] |
| BCTP 1:10 alone | 11 | 2.6 $cm^2$ white area |
| | 12 | 0.15 $cm^2$ white area |
| | 13 | no abnormalities observed |
| | 14 | 0.15 $cm^2$ white area |
| | 15 | 0.35 $cm^2$ white area |
| | 16 | no abnormalities observed |
| | 17 | 0.12 $cm^2$ white area |
| | 18 | no abnormalities observed |
| | 19 | 0.56 $cm^2$ white area |
| | 20 | 0.3 $cm^2$ white area Mean lesion size in BCTP 1:10 alone group = 0.60 $cm^2$ [3/10 (30%) with no abnormalities observed] |
| BCTP 1:100 alone | 21–30 | no abnormalities observed Mean lesion size in BCTP 1:100 alone group = 0 $cm^2$ [10/10 (100%) with no abnormalities observed] |
| TSB alone | 31–40 | no abnormalities observed Mean lesion size in the TSB alone group = 0 $cm^2$ [10/10 (100%) with no abnormalities observed] |

Re-isolation of *B. cereus* was attempted from skin lesions, blood, liver, and spleen. Skin lesions were cleansed with betadine followed by 70% sterile isopropyl alcohol. An incision was made at the margin of the lesion and swabbed. The chest was cleansed with betadine followed by 70% sterile isopropyl alcohol. Blood was drawn by cardiac puncture. The abdomen was cleansed with betadine followed by 70% sterile isopropyl alcohol. The skin and abdominal muscles were opened with separate sterile instruments. Samples of liver and spleen were removed using seperate sterile instruments. Liver and spleen samples were passed briefly through a flame and cut using sterile instruments. The freshly exposed surface was used for culture. BHI agar (Difco) was inoculated and incubated aerobically at 37° C. overnight.

TABLE 12

| Inoculum sc | ID # | Necropsy | *B. cereus* Re-isolation from site of skin lesion |
|---|---|---|---|
| *B. cereus* | 3 | 24 hours | skin lesion >300 cfu |
| 5.5 × $10^7$ | 6 | 48 hours | skin lesion >300 cfu |
| spores/mouse | 7 | 48 hours | skin lesion >300 cfu |
| in the | 8 | 72 hours | skin lesion 100 cfu |
| Untreated group | 9 | 72 hours | skin lesion 25 cfu |
| | 10 | 72 hours | skin lesion 100 |
| | 1 | 96 hours | skin lesion >300 cfu |
| | 4 | 96 hours | skin lesion >300 cfu |
| | 5 | 96 hours | skin lesion >300 cfu Mean CFU in Untreated Spore group = 214* *[6/9 (67%) > 300 CFU] |
| *B. cereus* | 48 | 48 hours | skin lesion 17 cfu |
| 2.8 × $10^7$ | 50 | 48 hours | skin lesion >300 cfu |
| spores/mouse | 46 | 72 hours | skin lesion >200 cfu |
| in the | 47 | 72 hours | skin lesion 100 cfu |
| BCTP 1:10 | 49 | 72 hours | skin lesion >300 cfu |
| treated group | 41** | 96 hours | skin lesion >300 cfu |
| | 42** | 96 hours | skin lesion 20 cfu |
| | 43 | | cultures not done |
| | 44 | 96 hours | skin lesion >300 cfu |
| | 45 | | cultures not done |
| | 46 | | cultures not done Mean CFU in BCTP 1:10 group = 192* *[3/8 (38%) > 300 CFU] |
| *B. cereus* | 48 | 48 hours | skin lesion 18 cfu |
| 1.8 × $10^7$ | 50** | 48 hours | skin lesion >300 cfu |
| spores/mouse | 52 | 72 hours | skin lesion 1 cfu |
| in the | 54 | 72 hours | re-isolation negative |
| BCTP 1:100 | 56 | 72 hours | skin lesion >300 cfu |
| treated group | 58 | 96 hours | skin lesion 173 cfu |
| | 59 | 96 hours | skin lesion 4 cfu |
| | 60 | 96 hours | skin lesion 6 cfu Mean CFU in BCTP 1:100 group = 100 *[2/8 (25%) > 300 CFU] |

**Although no lesions were present in these mice, organisms were removed from the injection site.

Pretreatment of both vegetative *B. cereus* and *B. cereus* spores reduce their ability to cause disease symptoms when introduced into experimental animals. This is reflected in the smaller size of skin lesions and the generally lower numbers of *B. cereus* recovered from the lesions. In addition, less frequent re-isolation of *B. cereus* from blood, liver, and spleen occurs suggesting that septicemia may be reventable.

SPECIFIC EXAMPLE 6

In Vivo Toxicity Study I

CD-1 mice were injected subcutaneously with 0.1 cc of the compounds of the present invention and observed for 4 days for signs of inflammation and/or necrosis. Dilutions of the compounds were made in sterile saline.

Tissue samples from mice were preserved in 10% neutral buffered formalin for histopathologic examination. Samples of skin and muscle (from mice which were injected with undiluted compounds) sent for histological review were reported to show indications of tissue necrosis. Tissue samples from mice which were injected with diluted compounds were not histologically examined. The following two tables show the results of two individual experiments.

TABLE 13

| Compound | Mouse ID # | Dilution | Observation |
|---|---|---|---|
| BCTP | 1326 | undiluted | necrosis |
| | 1327 | undiluted | no reaction |
| | 1328 | 1:10 | no reaction |
| | 1329 | 1:10 | no reaction |
| | 1324 | 1:100 | no reaction |
| | 1331 | 1:100 | no reaction |
| Saline | 1344 | | no reaction |
| | 1345 | | no reaction |

TABLE 14

| Compound | Mouse ID # | Dilution | Observation |
|---|---|---|---|
| BCTP | 1376 | undiluted | necrosis |
| | 1377 | undiluted | no reaction |
| | 1378 | 1:10 | no reaction |
| | 1379 | 1:10 | no reaction |
| | 1380 | 1:100 | no reaction |
| | 1381 | 1:100 | no reaction |
| Saline | 1394 | | no reaction |
| | 1395 | | no reaction |

Guinea pigs were injected intramuscularly (in both hind legs) with 1.0 cc of compounds of the present invention per site and observed for 4 days for signs of inflammation and/or necrosis. Dilutions of the compounds were made in sterile saline.

Tissue samples from guinea pigs were preserved in 10% neutral buffered formalin for histological examination. Tissue samples were not histologically examined.

TABLE 15

| Compound | Guinea Pig | Dilution | Observation |
|---|---|---|---|
| BCTP | 1023-1 | undiluted | no reaction |
| | 1023-2 | 1:10 | no reaction |
| | 1023-3 | 1:100 | no reaction |
| Saline | 1023-10 | | no reaction |

The results of In vivo Toxicity Study I show that subcutaneous and intramuscular injection of the compounds tested did not result in grossly observable tissue damage and did not appear to cause distress in the experimental animals.

SPECIFIC EXAMPLE 7

In Vivo Toxicity Study II

One group of Sprague-Dawley rats each consisting of five males and five females were placed in individual cages and acclimated for five days before dosing. Rats were dosed daily for 14 days. On day 0–13, for 14 consecutive days each rat in Group 1 received by gavage three milliliters of BCTP, 1:100 concentration, respectively. The three milliliter volume was determined to be the maximum allowable oral dose for rats. Prior to dosing on Day 0 and Day 7, each rat was weighed. Thereafter rats were weighed weekly for the duration of the study. Animals were observed daily for sickness or mortality. Animals were allowed to rest for 14 days. On Day 28 the rats were weighed and euthanized.

The mean weight results of the oral toxicity study are shown in Table 16. Mean weights for males and females on Days 0, 7, and 14, 21 and 28 and the mean weight gains from Day 0–Day 28, are also shown in Table 16. One rat died due to mechanical trauma from manipulation of the gavage tubing during dosing on Day 14. All surviving rats gained weight over the 28-day course of the study and there was no illness reported.

Thus, although tributyl phosphate alone is known to be toxic and irritating to mucous membranes, when incorporated into the emulsions of the present invention, these characteristics are not in evidence.

The BCTP emulsion, 1:100 concentration, was also tested for dermal toxicity in rabbits according to the protocols provided in 16 CFR §1500.3 (data not shown).

The emulsion was not irritating to skin in the animals tested.

TABLE 16

| Rat Number | Sex | Dose Volume mL | Body Weight (g) Day 0 | Body Weight (g) Day 7 | Body Weight (g) Day 14 | Body Weight (g) Day 21 | Body Weight (g) Day 28 | Weight Gain (g) Day 0–Day 28 |
|---|---|---|---|---|---|---|---|---|
| 9028 | M | 3 | 332.01 | 356.52 | 388.66 | 429.9 | 394.07 | 62.06 |
| 9029 | M | 3 | 278.62 | 294.65 | 296.23 | 310.7 | 392.6 | 113.98 |
| 9030 | M | 3 | 329.02 | 360.67 | 325.26 | 403.43 | 443.16 | 114.14 |
| 9031 | M | 3 | 334.64 | 297.04 | 338.82 | 357.5 | 416.89 | 82.25 |
| 9032 | M | 3 | 339.03 | 394.39 | 347.9 | 331.38 | 357.53 | 18.5 |
| MEAN WTS | | | 256.26 | 340.65 | 339.37 | 366.58 | 400.85 | 78.18 |
| 9063 | F | 3 | 302 | 298.08 | 388.66 | 338.41 | 347.98 | 45.98 |
| 9064 | F | 3 | 254.54 | 247.97 | 256.78 | 278.17 | 279.2 | 24.66 |
| 9065 | F | 3 | 225.99 | 253.81 | 273.38 | 290.54 | 308.68 | 82.69 |
| 9066 | F | 3 | 246.56 | 260.38 | 266.21 | 235.12 | 272.6 | 26.04 |
| 9067 | F | 3 | 279.39 | 250.97 | deceased | | | |
| MEAN WTS | | | 261.69 | 262.24 | 296.25 | 285.56 | 302.11 | 53 |

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims. All patents and other publications cited herein are expressly incorporated by reference.

We claim:

1. A method of inactivating a Gram positive bacteria comprising contacting said Gram positive bacteria with a bacteria-inactivating emulsion, such that said Gram positive bacteria is inactivated, wherein said bacteria-inactivating emulsion comprises an oil-in-water emulsion in the form of a discontinuous oil phase distributed in an aqueous phase with a surfactant stabilizer, said oil phase comprising an organic phosphate-based solvent and a carrier oil.

2. The method of claim 1 wherein said oil phase in said emulsion is composed of droplets having a mean particle size in the range from 0.5 to 5 microns.

3. The method of claim 1 wherein said surfactant is selected from the group consisting of Tween 20, Tween 80 and Triton X-100.

4. The method of claim 3 wherein said surfactant is Triton X-100.

5. The method of claim 1 wherein said organic phosphate-based solvent is selected from the group consisting of dialkyl phosphates and trialkyl phosphates.

6. The method of claim 5 wherein said trialkyl phosphate comprises tri-n-butyl phosphate.

7. The method of claim 1 wherein said carrier oil is selected from the group consisting of soybean oil, avocado oil, squalane oil, squalene oil, olive oil, canola oil, corn oil, rapeseed oil, safflower oil, sunflower oil, fish oils, flavor oils, water insoluble vitamins and mixtures thereof.

8. The method of claim 7 wherein said carrier oil comprises soybean oil.

9. The method of claim 1 wherein said gram positive bacteria is Bacillus.

10. The method of claim 1 wherein said gram positive bacteria is *Bacillus anthracis*.

11. A method of inactivating a bacterial spore comprising contacting said bacterial spore with a bacterial spore-inactivating emulsion, such that said bacterial spore is inactivated, wherein said bacterial spore-inactivating emulsion comprises an oil-in-water emulsion in the form of a discontinuous oil phase distributed in an aqueous phase with a surfactant stabilizer, said oil phase comprising an organic phosphate-based solvent and a carrier oil.

12. The method of claim 11 wherein said oil phase in said emulsion is composed of droplets having a mean particle size in the range of about 0.5 to about 5 microns.

13. The method of claim 11 wherein said surfactant is selected from the group consisting of Tween 20, Tween 80 and Triton X-100.

14. The method of claim 13 wherein said surfactant is Triton X-100.

15. The method of claim 11 wherein said organic phosphate-based solvent is selected from the group consisting of dialkyl phosphates and trialkyl phosphates.

16. The method of claim 15 wherein said trialkyl phosphate comprises tri-n-butyl phosphate.

17. The method of claim 11 wherein said carrier oil is selected from the group consisting of soybean oil, avocado oil, squalane oil, squalene oil, olive oil, canola oil, corn oil, rapeseed oil, safflower oil, sunflower oil, fish oils, flavor oils, water insoluble vitamins and mixtures thereof.

18. The method of claim 17 wherein said carrier oil comprises soybean oil.

19. The method of claim 11 wherein said bacterial spore is Bacillus.

20. The method of claim 11 wherein said bacterial spore is *Bacillus anthracis*.

21. A method of treating bacterial infection caused by a gram positive bacteria in a subject, said method comprising administering a bacteria-inactivating emulsion to said subject such that bacterial infection is treated, wherein said bacteria-inactivating emulsion comprises an oil-in-water emulsion in the form of an oil phase distributed in an aqueous phase with a surfactant stabilizer, said oil phase comprising an organic phosphate-based solvent and a carrier oil.

22. The method of claim 21 wherein said administration step further comprises administering said emulsion topically.

23. The method of claim 21 wherein said administration step further comprises administering said emulsion orally.

24. The method of claim 21 wherein said administration step further comprises administering said emulsion by means of a porous pad.

25. The method of claim 21 wherein said oil phase in said emulsion is composed of droplets having mean particle size in the range of about 0.5 to about 5 microns.

26. The method of claim 21 wherein said surfactant is selected from the group consisting of non-ionic and anionic surfactants.

27. The method of claim 26 wherein said surfactant is Triton X-100.

28. The method of claim 21 wherein said organic phosphate-based solvent comprises a trialkyl phosphate.

29. The method of claim 28 wherein said trialkyl phosphate comprises tri-n-butyl phosphate.

30. The method of claim 21 wherein said carrier oil consists essentially of a vegetable oil.

31. The method of claim 30 wherein said vegetable oil is soybean oil.

32. The method of claim 21 wherein the gram positive bacteria are Bacillus species.

33. The method of claim 21 wherein the gram positive bacteria is *Bacillus anthracis*.

34. The method of claim 21 wherein the gram positive bacteria is a bacterial spore.

35. The method of claim 21 wherein said bacteria-inactivating emulsion is non-toxic to the affected subject.

36. The method of claim 21 wherein said bacteria-inactivating emulsion is not irritating to the affected subject.

37. A method of inactivating a Gram negative bacteria comprising contacting said Gram negative bacteria with a composition comprising a bacteria-inactivating emulsion and a compound which enhances uptake of said emulsion into said bacteria's cells, such that said Gram negative bacteria is inactivated, wherein said bacteria-inactivating emulsion comprises an oil-in-water emulsion in the form of a discontinuous oil phase distributed in an aqueous phase with a surfactant stabilizer, said oil phase comprising an organic phosphate-based solvent and a carrier oil.

38. The method of claim 37 wherein said oil phase in said emulsion is composed of droplets having a mean particle size in the range of about 0.5 to about 5 microns.

39. The method of claim 37 wherein said surfactant is selected from the group consisting of Tween 20, Tween 80 and Triton X-100.

40. The method of claim 39 wherein said surfactant is Triton X-100.

41. The method of claim 37 wherein said organic phosphate-based solvent is selected from the group consisting of dialkyl phosphates and trialkyl phosphates.

42. The method of claim 41 wherein said trialkyl phosphate comprises tri-n-butyl phosphate.

43. The method of claim 37 wherein said carrier oil is selected from the group consisting of soybean oil, avocado oil, squalane oil, squalene oil, olive oil, canola oil, corn oil, rapeseed oil, safflower oil, sunflower oil, fish oils, flavor oils, water insoluble vitamins and mixtures thereof.

44. The method of claim 43 wherein said carrier oil comprises soybean oil.

45. The method of claim 37 wherein said gram negative bacteria are selected from the group consisting of Vibrio, Salmonella, Shigella and pseudomonas.

46. The method of claim 37 wherein said compound which enhances uptake of said emulsion into said bacteria's cells is selected from the group consisting of EDTA, DMSO and SDS.

47. The method of claim 37 wherein said compound is EDTA.

48. The method of claim 47 wherein said EDTA is at a concentration of about 50 to about 250 $\mu$M.

* * * * *